United States Patent [19]

Newkirk

[11] Patent Number: 4,850,955
[45] Date of Patent: Jul. 25, 1989

[54] BODY FLUID TRANSFER DEVICE

[75] Inventor: John B. Newkirk, Evergreen, Colo.

[73] Assignee: Codman & Shurtleff, Randolph, Mass.

[21] Appl. No.: 936,888

[22] Filed: Dec. 2, 1986

[51] Int. Cl.⁴ .............................................. A61M 27/00
[52] U.S. Cl. ........................................... 604/9; 604/8
[58] Field of Search ...................................... 604/8–10, 604/185; 137/510

[56] References Cited

U.S. PATENT DOCUMENTS

| | | | |
|---|---|---|---|
| 3,654,932 | 4/1972 | Newkirk et al. | 604/9 |
| 3,768,508 | 10/1973 | Schulte | 604/9 |
| 3,827,439 | 8/1974 | Schulte et al. | 604/9 |
| 4,240,434 | 12/1980 | Newkirk | 604/9 |
| 4,364,395 | 5/1984 | Redmond et al. | 137/510 |
| 4,464,168 | 8/1984 | Redmond et al. | 604/9 |
| 4,554,918 | 11/1985 | White | 604/10 |
| 4,588,394 | 5/1986 | Schulte et al. | 604/9 |
| 4,681,560 | 7/1987 | Schulte et al. | 604/8 |

Primary Examiner—Barry S. Richman
Assistant Examiner—T. J. Wallen
Attorney, Agent, or Firm—James E. Pittenger

[57] ABSTRACT

A biomedical implantable shunt is provided having an enlarged generally circular pump body and a perforated distal and proximal catheter attached to said body. The catheters are intended to have excess length so they can be cut to proper length as necessary to fit a specific patient. The pump body includes a vestibule at the outlet end directly connected to the distal catheter. A pair of one-way miter valves are provided within the pump body. The inlet valve is directly connected to the entrance provided for the proximal catheter while the outlet valve is positioned within the vestibule which is connected to the distal catheter. A longitudinal ridge is provided in the base member of the pump body with one end of the ridge positioned directly under the inlet valve to eliminate the possibility of the valve becoming sealed in the closed position during the pumping operation. Additional longitudinal as well as transverse ridges can be provided in the base section as well as the interior of the pump dome to provide strength and rigidity within the pump body. The pump body portion of the shunt is formed as a one-piece integral unit by means of injection molding. Two separate mold cores are provided which are cantilevered with the pump body core supported by the vestibule core. The vestibule core is in turn supported from the interior of the mold so as to hold both cores in proper position and alignment during the molding process. The inlet and outlet apertures for the proximal and distal catheters respectively, are sized according to the elasticity and tear-resistance of the materials used in the molding process so that the cores can be extracted from the article without tearing or otherwise injuring the pump body material.

11 Claims, 2 Drawing Sheets

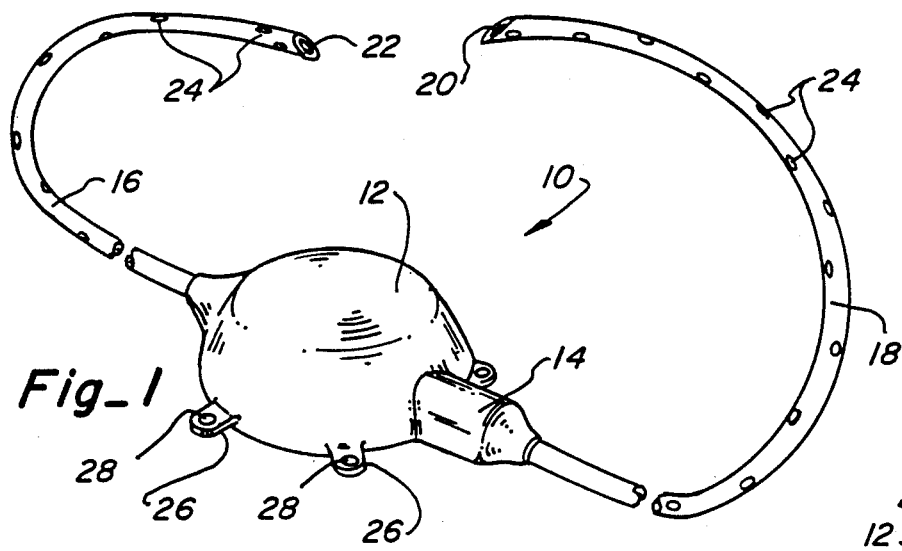
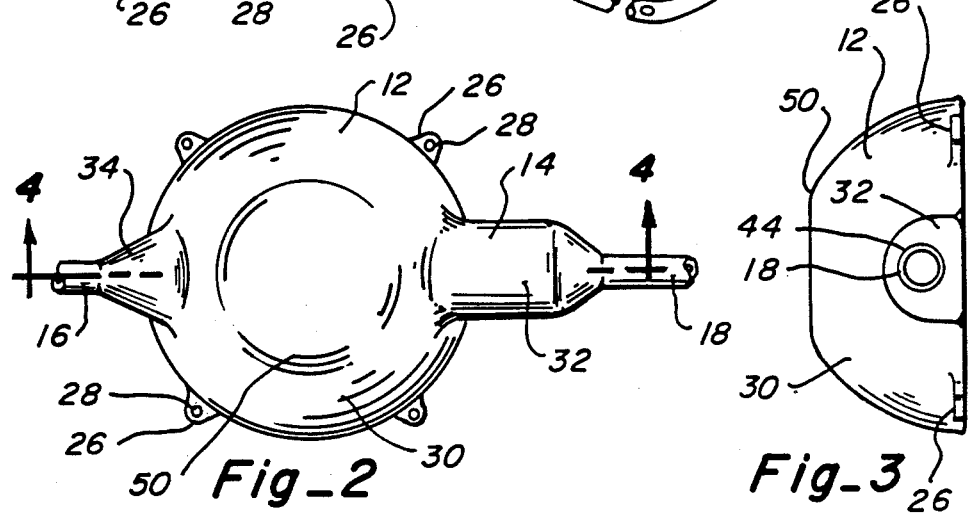
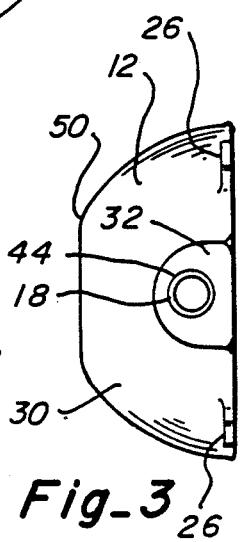
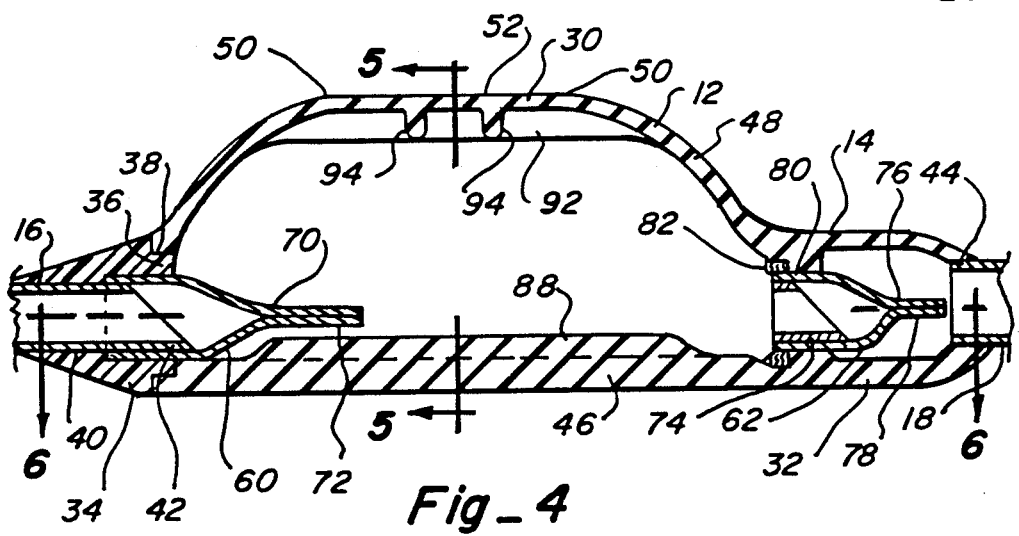

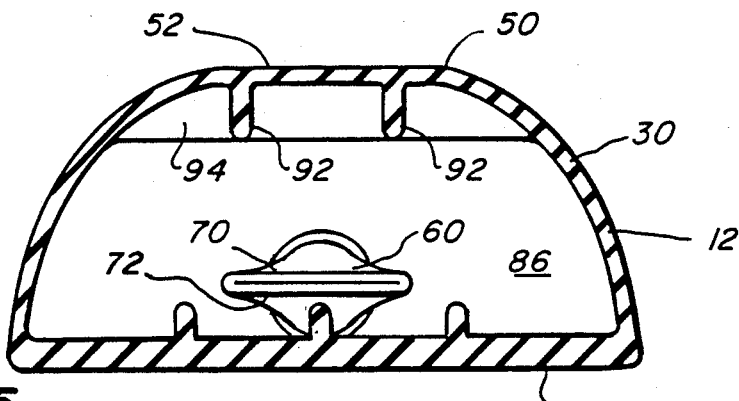
Fig_5
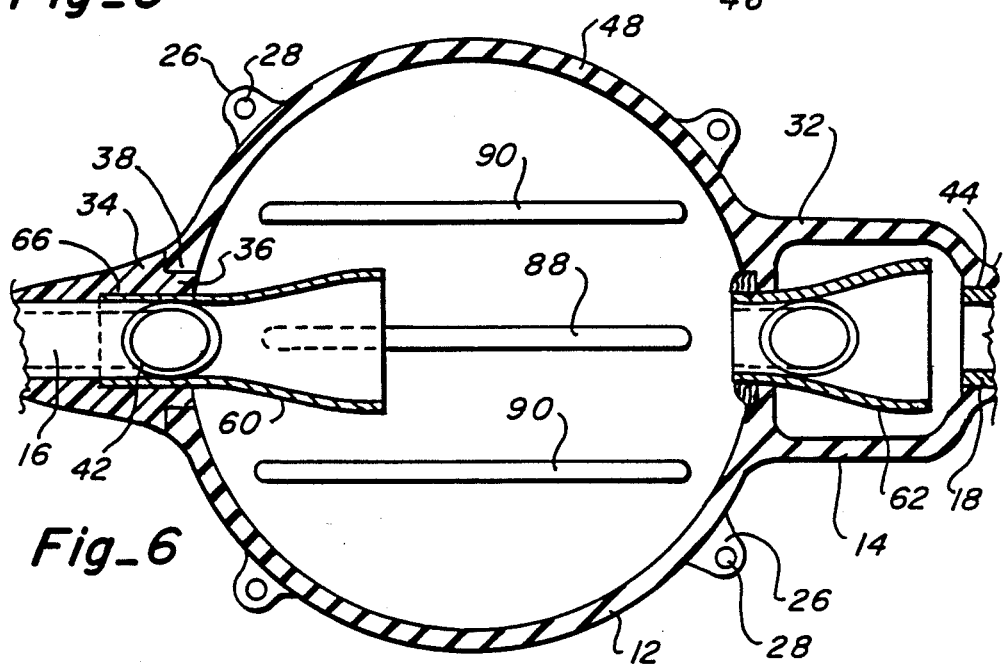
Fig_6
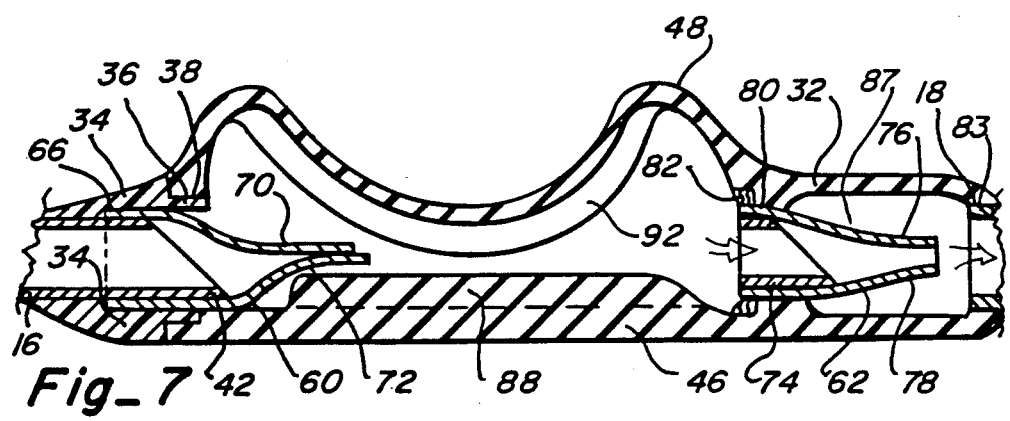
Fig_7

BODY FLUID TRANSFER DEVICE

FIELD OF THE INVENTION

This invention is directed to a medical shunt for drainage of fluid from one cavity within the human body to another or to a reservoir or other site outside of the body. It is more specifically directed to a medical shunt consisting of a double-valved flexible pump with proximal and distal catheters for transferring pleural effusion liquid from the pleural cavity to the peritoneal cavity for the diffusion and reabsorption of excess pleural fluids.

BACKGROUND OF THE INVENTION

The space between the visceral pleura (membrane surrounding each lung) and the parietal pleura (membrane lining the inside of the rib cage) normally contains a few milliliters of low-protein liquid, sometimes called pleural fluid. Normally this liquid is constantly being produced and absorbed and provides a lubricating function during the breathing process.

Under certain abnormal conditions such as the presence of a malignant carcinoma, infection or inflammation the net flow of pleural fluid within the visceral and parietal pleura becomes unbalanced resulting in the rapid accumulation of fluid in the pleural cavity. The result of the accumulation of this fluid causes a pathological compression of one or both lungs causing considerable difficulty or prevention of the breathing process in either one or both lungs. This excess fluid condition, called pleural effusion can cause the usual symptoms such as dyspnea, shortness of breath, chest pain and chronic cough. In the patient having lung cancer, a leading cause of pleural effusion, the fluid can be a major incapacitating feature greatly restricting the patient's activity, compromising his quality of life, and necessitating frequent hospitalizations for operative drainage of the fluid or periodic aspiration by the use of a catheter or needle, with attending risks of infection, sepsis and other pathological conditions.

The incidence of serious pleural effusion in the United States, as indicated by the number of hospital admissions where pleural effusion is the primary diagnosis, is more than 250,000 per year.

The traditional therapy for dealing with the excess pleural effusion includes repeated thoracentesis, surgical installation of a more or less permanent external drainage tube which leads the excess pleural fluid to a collection bag or reservoir outside of the body. In addition to the complete drainage of the pleural effusion, many times a sclerosing agent such as nitrogen mustard, atabrine or tetracycline is introduced to completely coat the visceral and parietal membranes so that these membranes will permanently adhere to each other to close and eliminate the pleural cavity. In this way the accumulation of fluid is prevented. This type of therapy produces pain and discomfort which can involve lengthy, repeated and costly hospitalization. This treatment frequently is accompanied by threatening or debilitating complications such as aggressive infections and loss of useful protein-rich body fluid. In addition this treatment has significant failure rates with respect to reducing the effusion itself.

Because of these considerable drawbacks in the prior therapies, a shunting device which is shown and disclosed in my prior U.S. Pat. No. 4,240,434 was developed to eliminate these types of problems. This device is a peritoneo-venous shunt which has perforated inlet and outlet catheters and a small roughly oval or cylindrical pump body having one or two valves to restrict liquid flow in only one direction. Although this shunt has worked well in certain situations it does not eliminate all of the problems which have been encountered especially when it is used as a pleuro-peritoneal shunt.

INFORMATION DISCLOSURE STATEMENT

The following patents which are listed and described are believed to be the most pertinent patents to this invention which are known by the inventor. This list is provided in order to comply with the inventor's duty to disclose to the Patent Office information which is material to the examination of this application.

The Newkirk patent (U.S. Pat. No. 4,240,434—mentioned above) shows a peritoneo-venous shunt which includes a perforated inlet catheter with an asymmetrical one-way valve attached to and contained within a small cylindrical pump body, a venous outlet catheter and a plurality of X-ray absorbing markers placed along the catheters for ascertaining their position within the patient by X-ray or fluoroscopic viewing. This device discloses a single asymmetrical flap valve which prevents the reverse flow of the drainage fluid. It has been found that the volumetric capacity of this shunt design is in practice insufficient when the device is used as a pleuro-peritoneal shunt. The asymmetrical construction of the flap valve provides a rubbing action which dislodges any particles from accumulating in the valve member which would tend to block the fluid flow or otherwise render the valve incompetent.

The Newkirk patent (U.S. Pat. No. 3,654,932) shows a different type of shunt, commonly used in hydrocephalic patients, which includes a small cylindrical pump body having a slit valve for restricting the liquid flow in only one direction. The cross-sectional configuration of the pump body is oval to reduce the overall height of the shunt when placed subcutaneously within the head of the patient.

The Redmond, et al. patent (U.S. Pat. No. 4,464,168) discloses a low profile shunt system which shows a resilient dome pump body having distal and proximal catheter passageways. The pump body includes a single disk-type one-way valve wherein the upper portion of the dome surface closes off certain passageways during pumping operation. The structure of this valve and pump is considerably different than that shown and disclosed by the applicant.

Another Redmond, et al. patent (U.S. Pat. No. 4,364,395) shows a similar type of low profile shunt which utilizes a dome-shaped pump body having a diaphragm valve provided within the dome for closing and cooperating with an inlet port area.

SUMMARY OF THE INVENTION

The present invention is a decided improvement over the prior art shunt devices which have been described hereinabove and used in the past. The present invention is a shunting device for draining pleural effusion subcutaneously from the pleural cavity to the peritoneal cavity where it can be absorbed. The device consists of a perforated proximal catheter where pleural fluid enters the shunt device. A compressible pump affixed to and downstream from the proximal catheter and a perforated distal catheter which leads the pleural fluid from the pump to the discharge site, usually within the peritoneal cavity. The ends of the catheters are cut at an acute angle to aid in the insertion of the catheters into the body cavities while the perforations are provided well up on the catheters from the free ends. The length of the catheters are intentionally left long so that the implanting surgeon can cut off the excess length at the time that the shunt is implanted. An integral longitudinal barium sulfate containing stripe incorporated in the wall of the catheters permit visualization by X-ray photographs or fluoroscopy to confirm proper positioning.

The most important area with respect to the present invention lies in the fluid pump which is intermediate to the proximal and distal catheters. It is extremely important to have a pump which will provide a considerable volumetric capacity while at the same time be capable of being subcutaneously implanted under the skin of the patient. Since the pump must be positioned over a rigid part of the body such as bone or cartilage in the rib cage, the size and shape of the pump body become critical to prevent tribonecrosis and pressure necrosis which can result from applying continuous pressure on the living tissues of the skin. Such pressure restricts or stops the supply of blood to the skin area causing the skin tissue to die. As a result of this condition abscesses and infection could become quite prevalent. Any shunt device which causes this condition would be unusable and unsatisfactory for the intended purpose.

In the present shunt it has been found that a truncated hyperbolic or partial dome configuration is quite desirable. This arrangement has produced unexpected useful results in that by making the upper portion of the dome flat and all of the transition lines tapered and filleted, subcutaneous compression stress on the skin tissue can be greatly minimized. At the same time the volumetric capacity of the pump can be maximized to increase the pump liquid flow for each pump cycle. This in itself is quite important in that the pump manipulation by the fingers must be held to an absolute minimum in order not to abrade or abuse the skin tissue during the pumping process. Abrasion of the skin tissue during the pumping process would mitigate the usefulness of the device. Thus, the manipulation pressure required to properly use the shunt, as well as the number of cycles that are required to eliminate the pleural effusion from the body cavity, are critical to the successful use and operation of the device.

Consistent with the statements made above concerning the reduced stresses caused by the pump, the present device includes a tandem arrangement for two one-way, asymmetrical flap or miter valves. One valve is positioned at the inlet to the pump body at the entrance of the proximal catheter, with the second valve positioned diametrically opposite in a vestibule which is attached directly to the outlet distal catheter. Both valves are positioned in the same direction to provide a one-way flow path through the shunt device. The use of this type of valve is desirable in that it allows flow through gravitational force or only minute pressure differentials to allow the fluid to flow naturally with spontaneous flow interruption in the opposite direction.

A plurality of individual tabs having an aperture therein or a narrow flange with a plurality of apertures is provided around the outer circumference of the pump body for suturing the body in proper location during implantation.

The method of manufacturing the shunt according to the present invention is novel from the standpoint that the pump body and its necessary cavities are molded into a substantially one-piece structure. A suitable silicon rubber such as Dow Corning Silastic (MDS144516) is used to form the pump body by means of injection molding. In this type of molding process a body core is provided to establish the internal hollow cavity provided within the main pump body. The small vestibule or chamber to support and protect the outlet valve is provided at one edge of the pump body with a separate core forming the interior of this vestibule. This smaller core serves several critical functions.

The vestibule core is supported within the cavity of the separable mold by the use of a cylindrical support rod which also forms the outlet aperture for attaching the distal catheter. In addition a second rod extends out the opposite side of the vestibule core from the support tube and extends into the main area of the pump body. The main body core is slidably mounted on the second support rod and is keyed to the tube to hold it in aligned position with the vestibule core and the mold itself. The second support rod is sized to provide the proper sized aperture for mounting the outlet miter valve. In this arrangement both the body and vestibule cores are cantilever supported and at the same time serve to support and position one another within the mold, with the core supports providing some of the molded features.

Once the molding process has been completed, the main body core is removed through an opening provided on the inlet side of the pump body. This opening is sized to allow the large body core to be extracted without tearing or stretching the side of the body beyond its elastic limit. The vestibule core is extracted in the opposite direction through the outlet opening which is also sized to permit this extraction without tearing or stretching the material at the opening beyond its elastic limit. Through this process a substantially one-piece flexible and reliable pump body is provided which will have an extended useful life far beyond that presently experienced in assembled prior art devices.

It has also been found desirable with this device to provide reinforcing ribs, longitudinal and possibly transverse, on the inner surfaces of the dome and flat base portion of the pump body. These ridges provide a useful stiffening of the dome and pump body. The added stiffness encourages the dome to quickly return to its original configuration during pumping, thereby hastening the pumping operation and also reducing the probability of inducing cracks and splits in the wall of the pump body. In addition it has been found desirable to provide a longitudinal ridge on the upper surface of the base portion directly below the inlet valve to prevent the inner surfaces of the pump dome and base from sealing against the miter valve which in turn prevents entrance of fluid on the intake portion of the cycle which may render the pump inoperable. Such a ridge also serves to beneficially stiffen the base of the pump body.

BRIEF DESCRIPTION OF THE DRAWINGS

This invention will be more readily understood from a reading of the following specification and by reference to the accompanying drawings forming a part thereof, wherein:

FIG. 1 is a perspective view of the pleuro-peritoneal improved shunt according to the present invention showing the proximal and distal catheters shortened for illustrative purposes;

FIG. 2 is a top plan view of the pump body;

FIG. 3 is an end view showing a vestibule for the outlet valve;

FIG. 4 is a cross-sectional view of the pump body taken along lines 4—4 of FIG. 2;

FIG. 5 is a cross-sectional view of the pump body taken along lines 5—5 of FIG. 4;

FIG. 6 is a cross-sectional plan view through the pump body taken along lines 6—6 of FIG. 4; and FIG. 7 shows a pictorial view of the pump body with the dome compressed showing fluid outlet flow.

DETAILED DESCRIPTION OF THE DRAWINGS

Turning now more specifically to the drawings, FIG. 1 shows a drainage apparatus or shunt device 10 according to the present invention which includes a truncated hyperbolic or domed pump portion 12 having an outlet vestibule 14, proximal inlet catheter 16 and distal outlet catheter 18. The catheters 16, 18 are formed from tubular silicon rubber which is medically compatible for implantation in the human body. The diameters of the catheters can be of any suitable size such as within the range of one-eighth to one-half inch. The catheters during the original manufacture are usually one to two feet in length which is intentionally long so that the shunt can be used on any patient regardless of his size.

The catheters are perforated by forming a number of holes usually diametrically through the catheter with every other hole approximately 90° to the previous hole in order to form a staggered hole pattern for at least six inches along the outer end of the catheters. The positioning and sizing of the holes allows the holes to remain open without accretion forming which could block fluid from entering the lumen of the catheter. Usually the perforated portion of the distal catheter is about twice the length of the proximal catheter to allow a sufficient number of holes to remain after the catheter has been properly sized.

Tabs 26 having apertures 28 are spaced around the circumference of the pump body 12 which allows the pump to be sutured into place subcutaneously to hold the pump in a secured position thereby preventing it from moving significantly. The final positioning of these tabs can be arranged to substantially fit the anticipated implantation area on the patient. It is also possible to have a narrow circular outer flange extending around the circumference of the pump body 12 with a number of holes or apertures provided in this flange to serve the same purpose as the tabs.

The pump body 12 is intended to have a low profile and is formed by truncating a hyperbolic dome. This portion is usually formed by a unique injection molding process which allows the structure to be formed in essentially three portions, namely, the domed portion 30, outlet vestibule 32 and inlet connector 34. While the central domed body portion 30 and vestibule 32 are formed as an integral unit the connector 34 is formed as a separate unit having a short extension or boss 36 which mates with an opening 38 provided in one end of the domed body 30. A central passageway 40 provided in the connector 34 allows the insertion and permanent attachment of the end 42 of the proximal catheter 16. The vestibule 32 at the opposite end of the body 30 has an aperture 44 which is sized to fit the outer diameter of the distal catheter 18. Through the aperture 44 the catheter 18 is permanently attached to the pump body 12.

The central body portion 30 is formed so as to have a generally flat base or planar section 46 and a dome shaped upper portion 48. The base section 46 is relatively thick having a thickness of approximately 3 millimeters. This dimension is approximately twice the thickness of the upper section forming the dome of the pump and is provided to lend rigidity and support to the overall pump structure. A chord line 50 is provided around the upper section of the dome 48 with the inner portion 52 of the dome within the chord line relatively flat and substantially parallel to the base 46. This flat area 52 forms a truncated section which reduces the overall height and minimizes the side profile of the pump section. This is a very important feature of the present invention in that it reduces the pressure which is placed on the internal tissues of the skin which prevents, the necrosis of the adjacent skin due to constant pressure being applied by the raised pump section. This lowered profile also minimizes and substantially eliminates the tendency for tribonecrosis which has been found to be caused by a subcutaneously implanted untrucated dome, making this invention a much more acceptable device for use with many types of patients.

In order to provide the required one-way flow of liquid through the pump body two valves 60, 62 such as asymmetrical, flat or miter type valves are provided. Valves suitable for this purpose are shown and described in my prior U.S. Pat. No. 4,240,434. For illustrative purposes the inlet valve 60 will be described with the understanding that the outlet valve 62 is formed in essentially an identical manner.

The end 42 of the proximal catheter 16 is cut at an angle of approximately 45° to the catheter axis. The one-way valve 60 is formed of soft, flexible, biocompatible material such as low durometer silicon rubber sheet consisting of two halves 70, 72. These two halves are joined, such as by cementing along the outer longitudinal edges, to form a flat, tubular section. It is also possible to mold this valve section as a one-piece flat, tubular portion wherein the two halves are molded together during the manufacturing process. One end of the valve section is positioned over the angled end 42 of the proximal catheter 16 and is cemented around its perimeter to the outer surface of the end 42 making a permanent bond. In this way the valve body 66 has an open end on the left side with the ends on the right side positioned adjacent to each other and in contact. Because of the mitered or angled cut provided on the end 42 of the catheter 16 the halves 70, 72 of the valve have different lengths and different prestressed tensions which provide a different rigidity in the separate halves. Thus, this type of valve is self-cleaning in that a rubbing movement occurs during reverse fluid pressure application.

The vestibule 32 is usually formed diametrically opposite the position of the inlet catheter 16 and valve 60. It is to be understood, however, that it is not necessary for the vestibule to be positioned diametrically opposite but it can be actually formed at any location around the circumference of the pump body 12 such as adjacent to the inlet. It is also possible that more than one vestibule and outlet valve can be provided along with a corresponding outlet and distal catheter for each vestibule. By the same token, it is possible to have more than one inlet valve and catheter depending upon the number and location of the cavities to be drained.

The asymmetrical one-way outlet valve 62 is formed essentially the same as the inlet valve 60. A small section of tubing 74 is provided with one end cut off at approximately a 45° angle. A flat tubular section is formed from halves 76, 78 and the tubing 74 is bonded within the left end of the valve formed by the halves 76, 78. The end of the rod 74 and the outer valve sections are positioned flush at the left edge. This valve is then inserted into the aperture 80 which is formed in the wall portion between the vestibule 32 and the pump body 30. A recessed shoulder 82 is provided around the perimeter of the aperture 80, which shoulder is to be filled with adhesive in order to permanently bond the valve 62 to the inside of the sidewall of the pump body 30. The end of the distal catheter 18 is inserted into the aperture 44 formed in the outer end of the vestibule 32 to complete the outer structure of the liquid-tight pump body 12.

As can be seen in FIG. 5, a cavity 86 is formed between the base member 46 and the upper dome member 48 of the pump body 30. Within the cavity 86 and formed longitudinally across the inner surface of the base member 46 is an elongated ridge 88. This ridge 88 can extend the full length of the body cavity 86 or can be limited to a shorter distance so long as a portion extends under the inlet miter valve 60. It is intended that this ridge will extend upwardly to but be slightly spaced from the lower half 72 of the valve 60. It is important that this ridge 88 extend under but does not touch the valve 60 when the latter is in its relaxed position. It is desirable in order to improve the reliability of the operation of the valve 60 to prevent the valve from becoming sealed between the base member 46 and the inside surface of the dome member 48 during compression of the dome during a pumping cycle. As shown in FIG. 7 the upper portion of the dome is partially inverted during the pumping cycle with the inlet valve 60 closed thus forcing the internal fluid out through the outlet valve 62 and the distal catheter 18 as shown by the arrows.

It is possible to provide additional longitudinal ridges 90 on the base member 46 as well as providing longitudinal ridges 92 in the interior surface of the upper dome section. These ridges are provided to add additional rigidity to the base member 46 as well as adding additional rigidity, strength and resilience during flexing of the dome portion 48 as seen in FIG. 7. Since the dome portion 48 must flex inwardly, striving to return to its normal position, the upper longitudinal ridges 92 provide additional strength and stiffness in the longitudinal direction to aid in restoring the dome member 48 to its original raised position. This action is quite important during the operation of the pump in that this restoring movement causes a reduced pressure within the cavity 86 which draws liquid through the proximal catheter 16 and the valve 60 to fill the cavity in preparation for the next pump cycle.

It is also possible to provide transverse ridges 94 in the upper portion of the dome section 48 to provide transverse rigidity to the dome. By the same token, transverse ridges can be provided on the inner or outer surface of the base member 46 to add additional strength to that member.

It is to be understood that this medical shunt can be used and positioned to withdraw fluid from any cavity within the body with the effluent from that cavity being dispersed to any other cavity in the body where it can be dissipated or to a reservoir outside of the body, if desired. If this device is utilized as a pleuroperitoneal shunt, wherein the effusion is withdrawn from the pleural or chest cavity, the pump body is normally positioned subcutaneously under the patient's skin and on top of the fifth or sixth rib. The proximal catheter is intended to be properly sized for length with the end cut at an acute angle such as 45° to the catheter axis and the catheter inserted through a short tunnel fabricated through an incision to introduce the catheter usually by a J-wire insertion needle into the pleural cavity at the most superior and posterior portion. The intent is to position the free end of the proximal catheter in the lowermost portion of the cavity so that most of the fluid collecting in the cavity can be drained. The pump itself is secured to the muscular fascia by sutures positioned in the suture holes 28 in the tabs 26 provided on the perimeter of the pump 12. The distal or outlet catheter is inserted into the peritoneal cavity by insertion through a tunnel formed through the abdominal muscle from the main incision. The distal catheter is also sized for proper length prior to insertion with the end of the catheter severed at an acute angle to aid in the insertion.

With the novel drainage apparatus 10 provided in the present invention it is possible to move relatively large volumes of liquid as digital pressure is applied to the flat top portion 52 of the pump 12. By pushing this section inward so that the dome member 48 contacts the ridges 88 and 90 provided on the surface of the base member 46 maximum volumetric displacement is obtained. By providing a pump having the following dimensions it is possible to move 10 milliliters or more of fluid in each pump cycle rather than the one or two milliliters which have been possible in the past. Thus, the use of the shunt according to the present invention makes it possible to reduce the number of pump cycles required by as much as 80% which greatly protects the patient and reduces the possibility of abrasion or injury to the skin during the pump manipulation.

Through experimentation an optimum size of pump body has been found. This configuration provides a diameter of approximately 50 millimeters with a height of approximately 22 millimeters. The base member has a thickness of 2.5 millimeters with the thickness of the dome member approximately 1.25 millimeters. The width of the ribs formed in the under side of the dome member 48 or the top surface of the base member 46 can vary from approximately one-half to one and one-half millimeters. It has been found that the proximal and distal catheters can have an outside diameter of approximately five millimeters with an inside diameter of approximately 1.5 to 2.5 millimeters. The vestibule section has a length of approximately 16.5 millimeters, height of approximately 10 millimeters and a width of 17 millimeters. As stated above, the volumetric capacity of a pump having these dimensions is approximately 10 millileters per pump cycle.

It has been found during the manufacture of this device that the molding process used for fabricating the pump body of the drainage apparatus is quite novel. It is desirable to form or mold the pump body as an integral unit in order to produce the part efficiently, to eliminate seams and sharp corners, and to reduce the possibility of fracturing or splitting the material due to fatigue. As a result it was found necessary to injection mold the pump body in a unique process utilizing a cantilevered double core arrangement. An injection mold was formed having an internal cavity with shape and dimensions as required for the outer configuration of the pump body and providing minimum dimensional tolerances. The outer surfaces of the unit must include fillets wherever two surfaces meet at an angle to reduce stress concentration and to improve reliability.

In order to form the base member 46 and dome member 48 a primary mold core is provided having outer dimensions to form the interior cavity 86. At the same time a smaller or vestibule core is provided which has dimensions to follow the interior cavity 87 of the vestibule 14. A cylindrical support rod having an outside diameter the same as aperture 44 is use to position and support the vestibule core within the mold cavity. In the same way a second rod having an outside diameter matching the aperture 80 is fixedly provided in the opposite side of the vestibule core and arranged long enough to slidably extend into an aperture provided within the pump body or primary core. Through a key arrangement between the rod and primary core, the primary core is held precisely within the interior mold cavity. In this way the pump body core is held in a rigid cantilevered position with respect to the vestibule and the outer support rod, thereby providing mutual support for the pump body and vestibule cores.

The mold is then closed and thermo-settable silicon rubber is forced into the mold and partially cured. After allowing the silicon rubber to set and partially cure the outer mold sections are separated and the shunt body is released from the mold. The vestibule core is extracted from the molded article through the opening 44 by carefully stretching the rubber in this area. The rod forming the aperture 80 slidably separates from the primary core with the two rods and vestibule core extracted carefully from the outlet opening in the vestibule. Once this has been accomplished the primary core is carefully extracted through the aperture 38 formed on the opposite side of the pump body from the vestibule. The aperture 38 is sized, depending upon the elasticity of the silicon rubber used, so that it will stretch sufficiently and without tearing to allow the safe removal of this core through the aperture. The connector 34 is molded separately from the pump body and is sized to fit the required aperture. In this way a substantially integral pump body is molded essentially as a one-piece unit.

This process of manufacturing is a vast improvement over the previous shunts that have been available in the past in that most of the previous articles have been fabricated from various individual pieces with the pieces cemented together to form the finished shunt device. Wherever the various pieces have been joined together that interface provides an area of possible separation which can threaten the reliability of the article and therefore the health and safety of the patient. Accordingly, the one-piece integral construction as provided in the present invention greatly improves the reliability and durability of the final product.

The shunt, according to the present invention, can be fabricated from any suitable silicon rubber material which is biologically compatible with the human body such as Dow Corning "Silastic". A suitable silicon rubber adhesive is used for cementing the parts of the pump together as well as for attaching the proximal and distal catheters. The dimensions which have been provided herein are directed to a preferred embodiment. These dimensions, however, can be varied as required and be sized for a particular patient. Thus, specially sized shunts according to the present invention can be provided if the intended patient is larger or smaller than normal or if the shunt is intended for a different usage such as bladder evacuation or for the controlled infusion of fluids into the body.

While a medical shunt for implantation in a human body has been shown and described in detail in this application, it is to be understood that this invention is not to be considered to be limited to the exact form disclosed. Changes in the detail and construction of the shunt may be made without departing from the spirit thereof.

What is claimed is:

1. A body fluid drainage device which can be implanted subcutaneously in a patient and operated by pressure applied through the skin of the patient, the drainage device comprising:

(a) a pump body means having an internal cavity, said pump body means having substantially flat base means and a hollow dome means having a perimeter which is sealingly attached around its perimeter to said base means, said hollow dome means having an outer central portion and an inside and outside surface, said hollow dome means further including a sidewall and a major diameter at the perimeter attached to said base means, said base means having an outer edge and is sized the same or slightly larger than the major diameter of said dome means, the outer central portion of said dome means being truncated to form a generally centered flat surface which is substantially parallel to said base means so as to reduce the height of said dome means in order to mitigate stresses applied to the skin of the patient, said pump body means having an inlet and an outlet opening positioned in the sidewall of said dome means, the outlet opening being formed as a hollow vestibule means formed in the sidewall of said dome means;

(b) at least first and second one-way vales are positioned within said pump body means, said first valve being mounted in said inlet opening with said second valve mounted within said vestibule means whereby liquid can only flow through said body means from said inlet through said outlet openings when a pressure differential across the device is sufficient to cause both valves to open and when the dome means is compressed toward the base means during a pumping cycle;

(c) a first catheter adapted to be implanted in a body cavity of the patient which has excess fluids, said catheter having first and second open ends, a substantial portion of said catheter adjacent to said first end being perforated to facilitate entry of the excess fluid from the body cavity to the pump body means, the second end of said catheter being sealingly attached to the inlet opening in said pump body means;

(d) a second catheter for transferring the fluid from the pump body means, an end of said second catheter being sealingly connected to the outlet opening of said outlet vestibule means to allow the fluid to pass out of said pump body means;

(e) said first one-way valve is a miter valve which includes top and bottom flattened adjoining portions having different mechanical characteristics so that superior external pressure depresses one portion of the valve more than the other so as to provide a differential movement of the flattened adjoining portions to provide a rubbing action to aid in preventing the valve from becoming clogged; and (f) at least one ridge is formed on the surface of said base means coinciding with the cavity of said pump body means, at least a portion of said ridge is positioned under said first one-way miter valve to prevent the valve from becoming sealed when the dome means is compressed during a pumping cycle.

2. A drainage device as defined in claim 1 wherein said pump body means and both catheters are formed from a silicon rubber.

3. A drainage apparatus as defined in claim 1 wherein said ridge formed on the inner surface of said base means is adapted to add rigidity and stiffness to said base means for improving the function of said pump body means.

4. A drainage device as defined in claim 1 wherein one or more ridges are formed on the inner surface of said dome means, said ridges being aligned substantially longitudinally along the line between the inlet and outlet openings whereby the strength and support of the dome means is increased to allow the dome means to return to its original position after being compressed.

5. A drainage device as defined in claim 1 wherein said base means and dome means are formed substantially in a circular configuration having a diameter which is within the range of 40 to 60 millimeters and an overall height of between 20 to 24 millimeters.

6. A drainage device as defined in claim 5 wherein the size of the cavity of the pump means is selected so that a minimum of 10 millimeters of fluid is moved through the outlet opening of said pump body means upon each compression of said dome means.

7. A drainage device as defined in claim 1 wherein attaching means is secured to the edge of said base means, said attaching means being adapted to hold the device in proper position within a patient by sutures.

8. A drainage device as defined in claim 7 wherein said attaching means includes one or more tabs which are spaced around the edge of said base means, each of said tabs having a hole provided centrally therein for suturing the device in place.

9. A drainage device as defined in claim 1 wherein the flat surface of said dome means has a diameter which is the same as or greater than one-half of the maximum diameter of said dome means.

10. A drainage device as defined in claim 1 wherein the thickness of said base means is at least twice the thickness of the sidewall of said dome means.

11. A drainage device as defined in claim 1 wherein said dome means, base means and vestibule means are molded as a one-piece unit, the inlet opening into said pump means being formed as an inlet aperture in the sidewall of said dome means, a connector means having an inner and outer end and a through passageway formed therein, said inner end of the connector means being adhesively mounted in said inlet aperture to enclose said aperture, and said first catheter is fixedly attached to the outer end of said connector means while the first one-way vavle is connected to the inner end of said connector means.

* * * * *